(12) United States Patent  
Oudovikine

(10) Patent No.: US 8,082,799 B2
(45) Date of Patent: Dec. 27, 2011

(54) METHOD OF FORECASTING THE LIFETIME OF STRUCTURAL PARTS

(75) Inventor: Alexandre Oudovikine, Thornhill (CA)

(73) Assignee: Paradigm Shift Technologies Inc., Toronto (CA)

( * ) Notice: Subject to any disclaimer, the term of this patent is extended or adjusted under 35 U.S.C. 154(b) by 25 days.

(21) Appl. No.: 12/515,698

(22) PCT Filed: Oct. 24, 2007

(86) PCT No.: PCT/CA2007/001893
§ 371 (c)(1),
(2), (4) Date: Sep. 22, 2009

(87) PCT Pub. No.: WO2008/061337
PCT Pub. Date: May 29, 2008

(65) Prior Publication Data
US 2010/0064819 A1    Mar. 18, 2010

Related U.S. Application Data

(60) Provisional application No. 60/859,957, filed on Nov. 20, 2006.

(51) Int. Cl.
*G01L 1/24*  (2006.01)
*G01N 3/32*  (2006.01)
(52) U.S. Cl. .......................................... 73/800; 73/810
(58) Field of Classification Search .............. 73/810, 73/800
See application file for complete search history.

(56) References Cited

U.S. PATENT DOCUMENTS

| | | |
|---|---|---|
| 2,294,897 A | 9/1942 | Ellis |
| 3,005,332 A | 10/1961 | McClintock |
| 3,433,060 A | 3/1969 | Ives et al. |
| 3,715,915 A | 2/1973 | Williams |
| 3,979,949 A | 9/1976 | Smith |
| 4,015,465 A | 4/1977 | Scott |
| 4,179,940 A * | 12/1979 | Oertle et al. ............... 73/808 |
| 4,265,120 A | 5/1981 | Morris et al. |
| 4,625,567 A | 12/1986 | Frayer, Jr. et al. |
| 4,869,113 A | 9/1989 | Sarrazin |
| 5,018,389 A | 5/1991 | Mraz |
| 5,531,123 A | 7/1996 | Henkel |

(Continued)

OTHER PUBLICATIONS

Office Actions and Response Corresponding to U.S. Appl. No. 11/875,206, Mailed Beginning Apr. 10, 2009.

(Continued)

*Primary Examiner* — Lisa Caputo
*Assistant Examiner* — Jonathan Dunlap
(74) *Attorney, Agent, or Firm* — Greenlee Sullivan P.C.

(57) ABSTRACT

A method is provided for determining the extent of cyclic stress fatigue suffered by a component comprising the steps of: (i) obtaining a gauge material which undergoes a continued progressive/cumulative and quantifiable change in at least one of its physical properties in response to repeated strain cycles applied to the gauge material, the quantifiable change being indicative of both degree of strain and number of cycles incurred during the repeated strain cycles; (ii) determining a correlation between an extent of the quantifiable change in the gauge material and an effect on said component of a corresponding number and degree of strain cycles; (iii) affixing the gauge material to said component to subject the gauge material to any strain encountered by an adjacent portion of the component; (iv) at least periodically determining the extent of said quantifiable change to the gauge material to determine the extent of cyclic stress fatigue undergone by the component.

8 Claims, 7 Drawing Sheets

U.S. PATENT DOCUMENTS

| | | | |
|---|---|---|---|
| 6,240,783 | B1 | 6/2001 | McGugin et al. |
| 6,592,502 | B1 | 7/2003 | Phillips |
| 7,299,678 | B2 | 11/2007 | Atherton |
| 7,515,781 | B2 | 4/2009 | Chimenti et al. |
| 2005/0273277 | A1 | 12/2005 | Ridnour et al. |
| 2007/0276294 | A1 | 11/2007 | Gupta et al. |
| 2008/0262754 | A1 | 10/2008 | Oudovikine |
| 2010/0299086 | A1 | 11/2010 | Oudovikine |

OTHER PUBLICATIONS

International Search Report for PCT/CA2007/001893 Mailed Feb. 7, 2008.

Written Opinion for PCT/CA2007/001893 Mailed Feb. 7, 2008.

International Preliminary Report on Patentability for PCT/CA2007/001893 Mailed Mar. 19, 2009.

* cited by examiner

TOP VIEW

SIDE VIEW

TESTING OBJECT (SPRING) WITH INTEGRAL STRAIN GAUGES

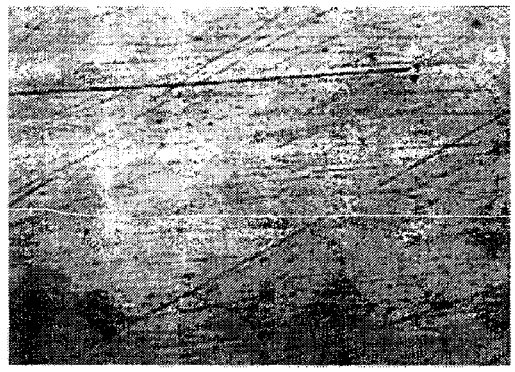
FIGURE 4  (R0)
FIGURE 5  (R1)
FIGURE 6  (R2)
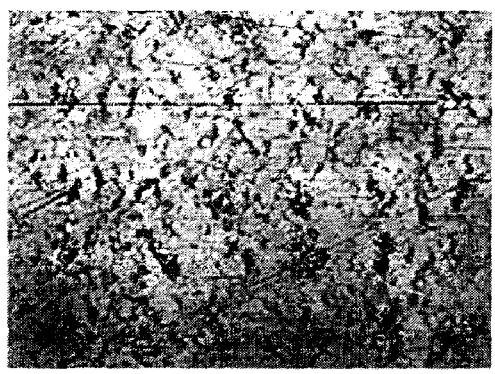
FIGURE 7  (R3)
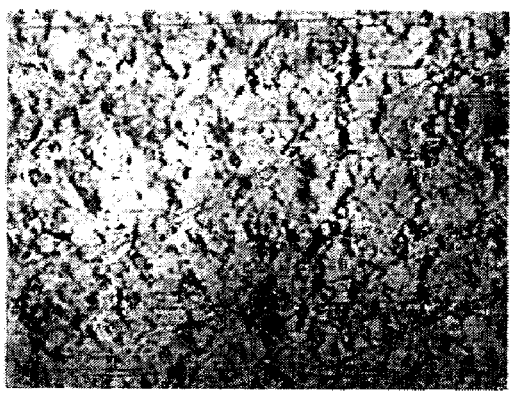
FIGURE 8  (R4)
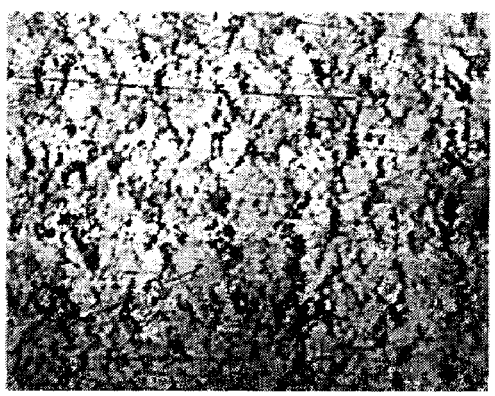
FIGURE 9  (R5)

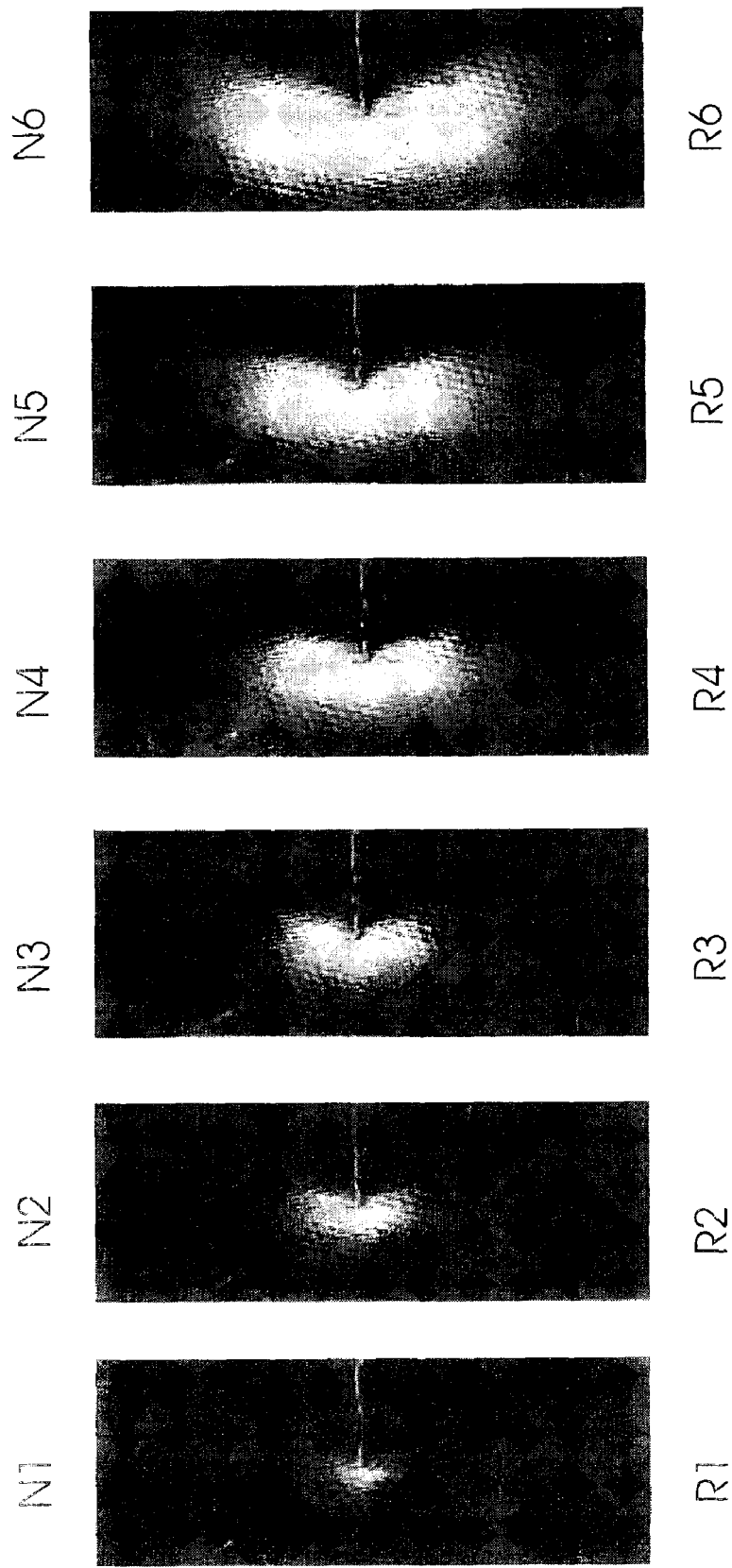

METHOD OF FORECASTING THE LIFETIME OF STRUCTURAL PARTS

FIELD OF THE INVENTION

This invention relates generally to mechanical testing. More particularly, this invention relates to methods of determining the lifetime of a machine part or component which is subject to cyclic stress.

BACKGROUND OF THE INVENTION

When a component is subject to sufficient stress forces it reacts by undergoing dimensional change, referred to as "strain". Stress and strain are related by the "Modulus of Elasticity" of the material of said component and accordingly, reference to one is indirectly a reference to the other.

Stress and strain have an indelible effect on the material at the microscopic and possibly even molecular level. For small amounts of stress/strain within the elastic range of the material, the effect of each stress/strain cycle is virtually negligible. Repeated stress/strain cycles have a cumulative effect causing the component to waken and eventually fail. The number of cycles to failure generally is a function of the amount of force (stress) applied. The greater is the stress per cycle the fewer are the cycles to failure.

Strain can be measured with a conventional electrical strain gauge. Such a gauge varies in resistance depending on loading (i.e. the amount of strain) but after loading it reverts to its unloaded state. Hence a strain gauge will only provide information on a given loading cycle rather than a history of the loading. Accordingly, a strain gauge on its own is not useful in predicting the remaining life of the component.

While a strain gauge could be augmented with a recording apparatus (for example a microprocessor) for recording loading history, this is generally impractical and in many applications impossible. For example if one wishes to monitor the loading history of a gear or a spring encased in a housing, there is no way in which to connect electrical leads to the strain gauge.

Accordingly it is an object of the present invention to provide an apparatus and a method for determining the extent of cyclic stress fatigue suffered by a component which doesn't require electrical connection or continued monitoring and tallying of each loading cycle.

SUMMARY OF THE INVENTION

A method is provided for determining the extent of cyclic stress fatigue suffered by a component comprising the steps of:
(i) obtaining a gauge material which undergoes a continued progressive/cumulative and quantifiable change in at least one of its physical properties in response to repeated strain cycles applied to the gauge material, the quantifiable change being indicative of both degree of strain and number of cycles incurred during the repeated strain cycles;
(ii) determining a correlation between an extent of the quantifiable change in the gauge material and an effect on said component of a corresponding number and degree of strain cycles;
(iii) affixing the gauge material to said component to subject the gauge material to any strain encountered by an adjacent portion of the component;
(iv) at least periodically determining the extent of said quantifiable change to the gauge material to determine the extent of cyclic stress fatigue undergone by the component.

Step (ii) above may be carried out by:
(ii-a) applying the gauge material to a test part;
(ii-b) cyclically applying a first known load ($T_1$) to the test part and monitoring the total number of load cycles (N);
(ii-c) examining the gauge material after step (ii-b) and determining and recording the amount of reaction (R) of the gauge material;
(ii-d) repeating (ii-b) and (ii-c) for further load cycles;
(ii-e) determining the relationship between change in number of cycles (N) and amount of change in gauge material ($\Delta R$) according to the formula:

$$\frac{\Delta R}{N} = V_1$$

where $V_1$ represents the relationship between N and $\Delta R$ at load $T_1$.
(ii-f) continuing to apply, after step (ii-e), the cyclical loading to the part until part failure and recording the number of cycles until failure ($N_{f1}$);
(ii-g) repeating (ii-a) to (ii-f) for different loads $T_2 \rightarrow T_x$ and determining the relationship ($V_2 \rightarrow V_x$) between change in gauge reaction ($\Delta R$) and the number of loading cycles (N) to establish known correlations and to establish the number of cycles to failure at each load ($N_{f2} \rightarrow N_{fx}$).

Step (iv) may be carried out carried out by:
(iv-a) inspecting the gauge material and determining the amount of gauge reaction at the time of inspection ($R_i$);
(iv-b) loading the part for a predetermined number of loading cycles ($N_p$);
(iv-c) inspecting the gauge material after (iv-b) and determining the amount of gauge reaction ($R_p$);
(iv-d) determining the relationship ($V_{det}$) between change in gauge reaction ($R_{i+p} - R_i$) and the number of known loading cycles ($N_p$) according to the formula:

$$\frac{R_{i+p} - R_i}{N_p} = \frac{\Delta R}{N_p} = V_{det}$$

(iv-e) comparing the relationship ($V_{det}$) in step (iv-d) with known correlations for the part ($V_1 \rightarrow V_x$) and selecting the closest to matching known correlation ($V_m$);
(iv-f) determining from the selected correlation ($V_m$) the load ($T_m$) corresponding thereto;
(iv-g) determining from the selected correlation ($V_m$), the number of elapsed cycles ($N_e$) corresponding to the gauge reaction ($R_{i+p}$) in step (iv-c);
(iv-h) determining from the selected correlation the number of cycles to failure ($N_{fm}$) at the load ($T_m$) determined in step (iv-f);
(iv-i) subtracting the results ($N_e$) in step (iv-g) from the results ($N_{fm}$) in step (iv-h) to determine the number of remaining cycles ($N_r$) i.e. ($N_{fm} - N_e = N_r$).

Alternatively, where the part has experienced a known number of cycles at inspection (Ni) step (iv) may be carried out by:
(iv-i) inspecting the gauge material and determining the amount of gauge reaction at the time of inspection ($R_i$);

(iv-ii) determining from the known correlations the load ($T_m$) corresponding to the amount of gauge reaction at the time of inspection ($R_i$) and the known number of cycles ($N_i$);

(iv-iii) determining from the known correlations the number of cycles to failure ($N_{fm}$) at the respective load ($T_m$); and, (iv-iv) subtracting the known number of cycles ($N_i$) from the number of cycles to failure ($N_{fm}$) to determine the number of remaining cycles ($N_r$) (i.e. $N_{fm}-N_i=N_r$).

DESCRIPTION OF DRAWINGS

Preferred embodiments of the present invention are described below with reference to the accompanying illustrations in which:

FIG. 4 is a photomicrograph of a testing surface of the integral strain gauge strip of FIG. 1 before an initial test;

FIG. 5 is a photomicrograph showing degree of reaction (R1) of the testing surface of the integral strain gauge strip of FIG. 1 at a first time interval, (t1) or after a number of loading cycles (N1) at a constant loading (T1);

FIG. 6 is a photomicrograph showing degree of reaction (R2) of the testing surface of the integral strain gauge strip of FIG. 1 at a second time interval, (t2) or after a number of loading cycles (N2) where (T1) remains constant;

FIG. 7 is a photomicrograph showing degree of reaction (R3) of the testing surface of the integral strain gauge strip of FIG. 1 at a third time interval, (t3) or after a number of loading cycles (N3) where (T1) remains constant;

FIG. 8 is a photomicrograph showing degree of reaction (R4) of the testing surface of the integral strain gauge strip of FIG. 1 at a fourth time interval, (t4) or after a number of loading cycles (N4) where (T1) remains constant;

FIG. 9 is a photomicrograph showing degree of reaction (R5) of the testing surface of the integral strain gauge strip of FIG. 1 at a fifth time interval, (t5) or after a number of loading cycles (N5) where (T1) remains constant;

DESCRIPTION OF PREFERRED EMBODIMENTS

Figure 1:
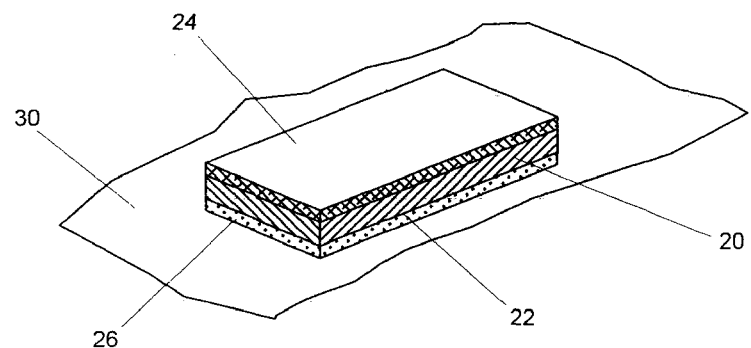
FIG. 1 is a perspective view of an integral strain gauge strip according an embodiment of the present invention.
Figure 2:
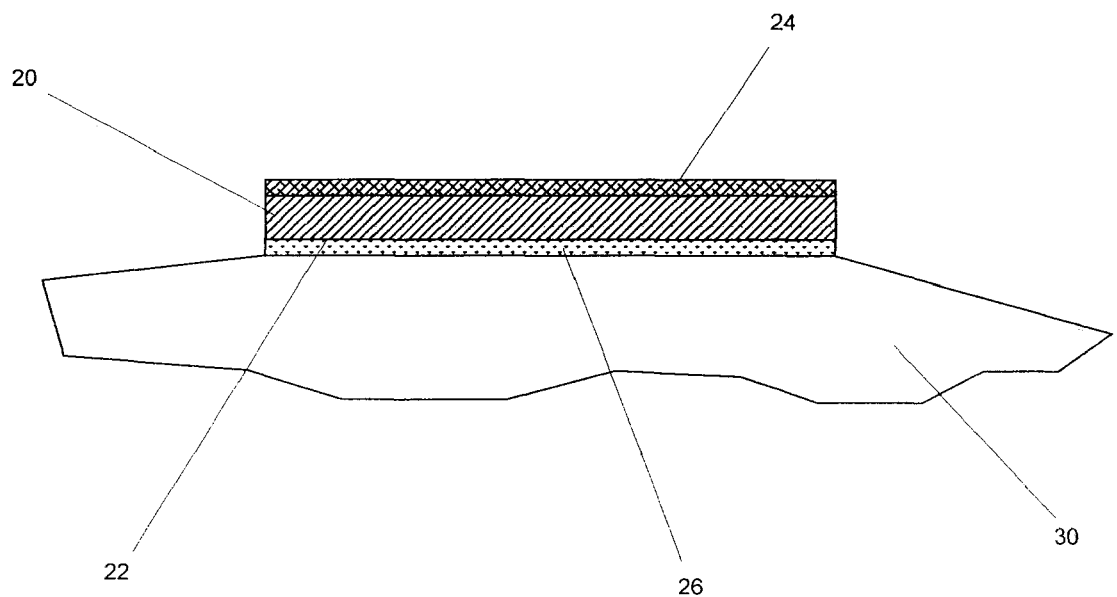
FIG. 2 is a front elevation of the integral strain gauge strip of FIG. 1 applicced to a component or part.
Figure 3:
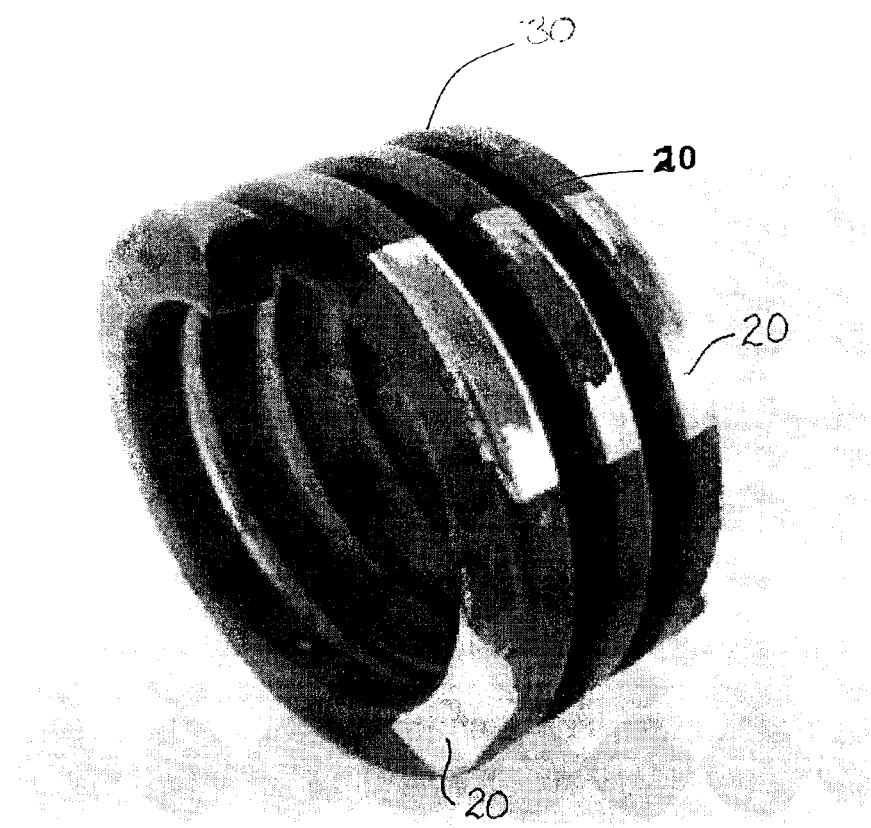
FIG. 3 is a perspective view of the integral strain gauge strip of FIG. 1 applied to a testing object (spring)

According to the present invention, as illustrated in FIGS. 1-3, a gauge material 20 is selected which undergoes a progressive, cumulative and quantifiable change in at least one of its physical properties in response to repeated strain cycles applied thereto. The gauge should be of a form and dimensions to be attachable to a component or a part 30 being monitored. For example the strain gauge 20 illustrated is in the form of a strip having substrate 22 with a reflective coating 24 on one face and affixing means such as an adhesive 26 on its opposite face.

The reflective coating 24 diminishes in reflectivity as the strain gauge 20 is repeatedly stressed. The diminishment of reflectivity may be caused by microstructural changes of either or both the substrate and the reflective coating.

The reflective coating 24 may simply be an outer surface of the substrate 22. The strain gauge 20 may therefore be a metal foil strip of 10 to 15 μm thickness glued to or plated on the component 30. Suitable metals include, without limitation, aluminum, silver, copper, gold, alloys thereof and composite materials.

The change in property described below is microstructure which may be monitored by monitoring reflectivity. It is expected that other physical properties could be monitored, such as for example resistivity and microhardness. Furthermore, although metal foils are the presently preferred embodiment, non-metallic materials including, without limitation, plastics and composite materials may also be acceptable at least for some applications.

FIG. 3 illustrates a strain gauge 20 applied to a part 30 wherein the part 30 is a coil spring. FIGS. 4 through 9 illustrate how the microstructure (and hence the reflective properties) of the surface 24 of a representative gauge 20 changes in response to continued cyclic stressing of the gauge 20. FIG. 4 shows a minimal reaction. FIGS. 5 through 9 show how the microstructure of the surface 24 changes after a progressive number of loading cycles N or after progressive time intervals t at a given load T1. By way of reference the change in microstructure (or other monitored property) will be referred to as the "degree of reaction" and assigned reference "R". Hence FIGS. 4 through 9 show the degree of reaction from the original surface R=Ro=O through R=R5 at a fifth time interval t5 or number of cycles N5. R may be expressed as a percentage. Hence Ro would be 0% with 100% indicating that the surface 24 or other monitored property has achieved its maximum possible degree of change.

The degree of change is a function not only of the number of cycles N or time t but also a function of the amount of load T per cycle. R may reach 100% well before part failure. In order to "calibrate" the gauge, a series of calibration tests using cyclic loading are carried out at different load levels. The cyclic loading is periodically interrupted, the time/number of cycles (t/N) are recorded as is an estimate of the degree of change from Ro. The testing is continued to failure for each loading T and the number of cycles to failure Nf is recorded.

Figure 10:
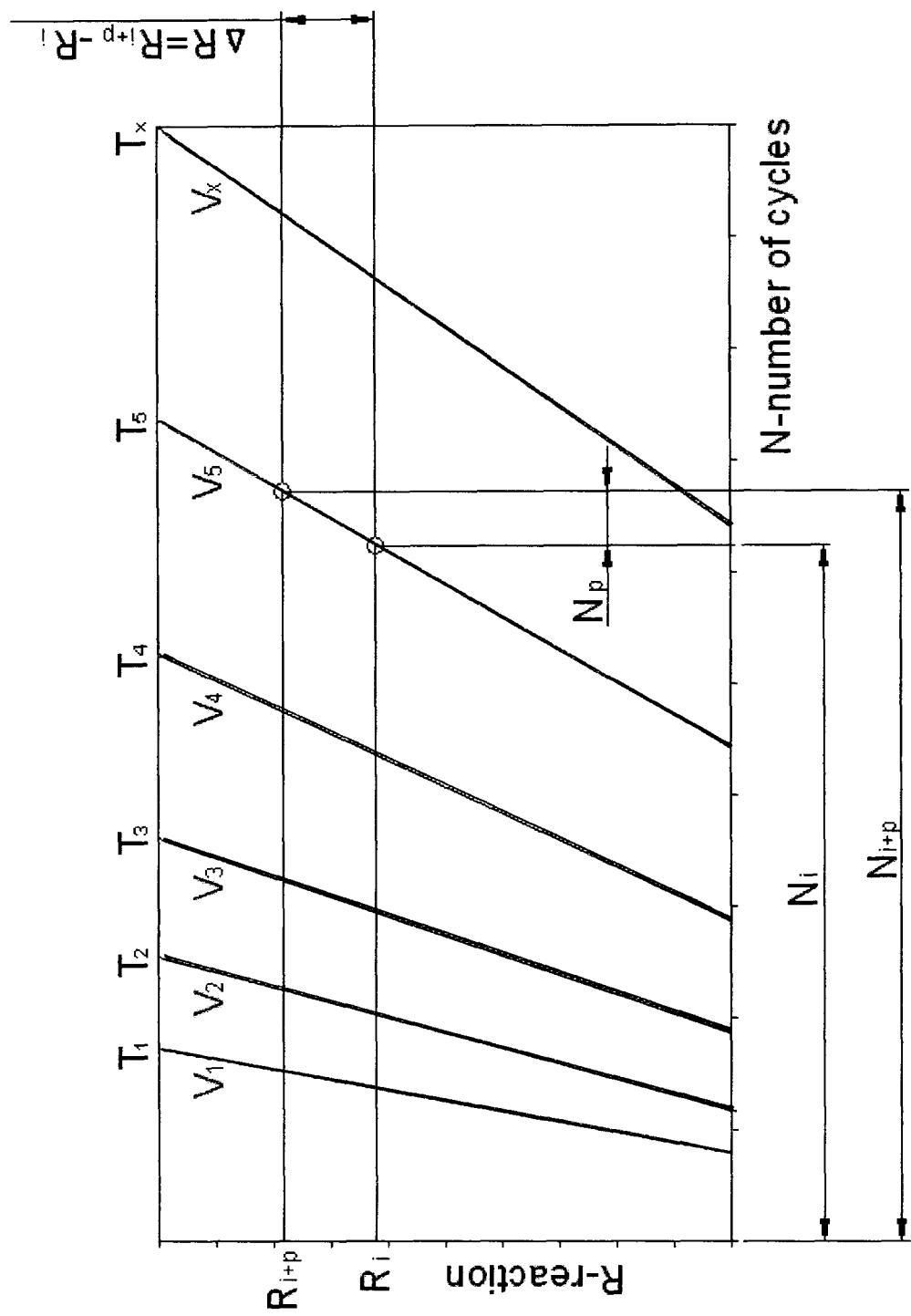
FIG. 10 is a graph showing gauge reaction (R) as a percentage versus number of cycles (N) plotted for various loadings (T1-T6)

The "calibration" results may be presented in any suitable manner such as graphic plots of R v. N with a different curve being plotted for each loading T. FIG. 10 is representative of such a graph for six loadings, T1-T6. Each curve in effect shows the relationship "V" between the number of cycles (N) and the amount of change (ΔR) of the gauge material. This may be expressed as:

$$\frac{\Delta R}{N} = V$$

In the case of the FIG. 10 example, the first curve might for example be the result of a series of tests carried out at $T_1$ which are reflected by the photomicrographs comprising FIGS. 4-9.

"Calibration" refers to determining how each gauge material responds to different cyclic loadings and to determine the different values for V for each gauge material and its respective part. The calibration may be carried out on test specimens which are not actual components or parts 30.

Figure 12:
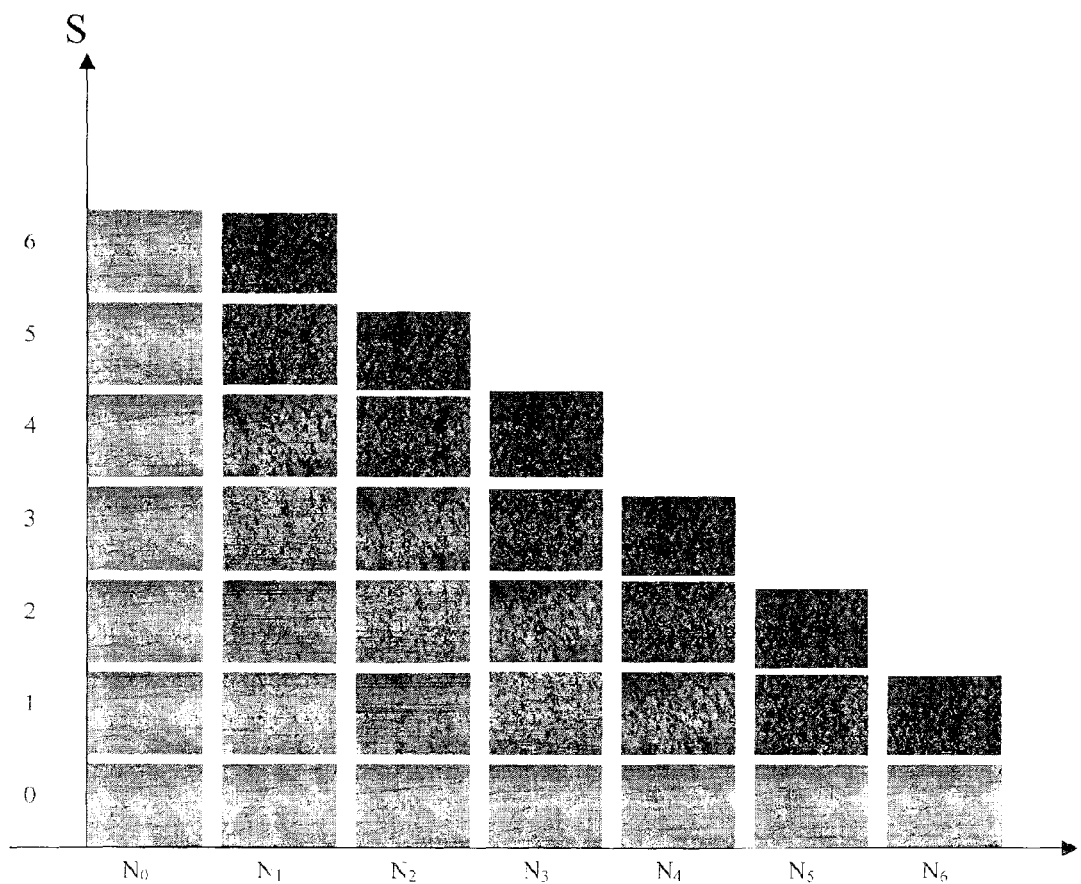
FIG. 12 is a series of photomicrographs arranged in strain (S) versus number of cycle (N) coordinates illustrating gauge reaction (R) as a function of (N) and (S); and, FIGS. 13 through 18 illustrate respectively gauge reaction R1 to R6 for differing numbers of strain cycles (N1 to N6) at a given load Tg for a gauge made of composite material.

FIG. 12 shows how degree of reaction (R) varies with strain (S). It can be seen that as strain (S) increases the number of cycles (N) required to effect a given change (R) diminishes.

Figure 11:
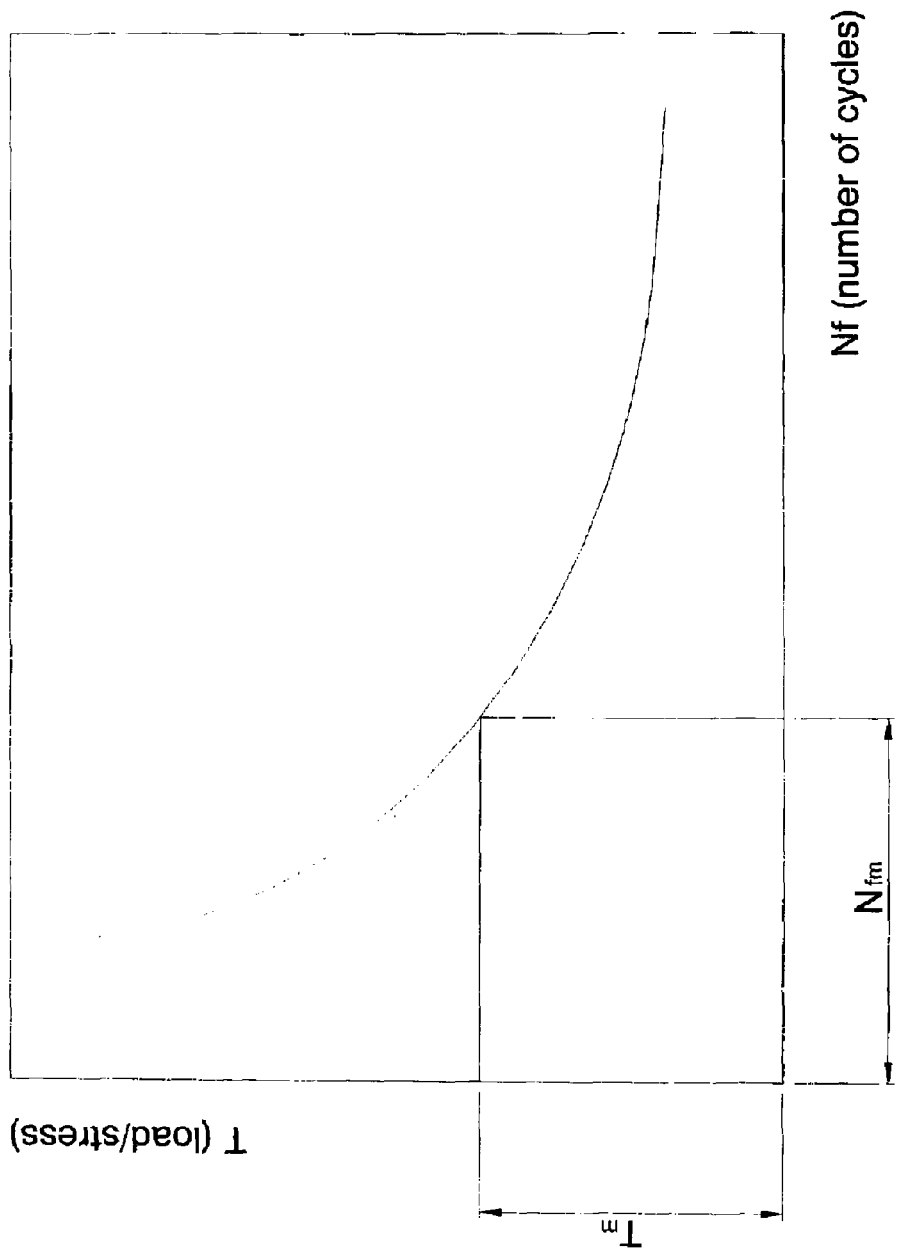
FIG. 11 is a graph of loading (T) versus number of cycles (N) showing number of cycles to failure (Nf).

A plot may also be made, as illustrated in FIG. 11 of number of cycles to failure (Nf) for each loading level (T).

How the gauge 30 may be used in predicting remaining life of the component or part 30 depends on what information is known about the part's loading history. For example, if the number of cycles or time is known at inspection (Ni or ti) then inspecting the gauge 20 and determining the amount of gauge reaction at the time of inspection (Ri) will indicate, from FIG. 10, which loading curve of T1-T6 best matches (Tm) with the number of cycles (Ni). One can then simply determine (FIG. 11) the number of cycles to failure (Nfm) for the loading curve (Tm) and subtract Ni from Nfm to calculate the remaining number of cycles (Nr) according to the formula:

$$N_{fm} - N_i = N_r$$

Where the total number of cycles is unknown, further testing is required to determine the loading history. This may be achieved by inspecting the gauge material 30 and determining the amount of gauge reaction at the time of inspection (Ri). The part 30 may then be subjected to an additional predetermined number of loading cycles Np. For example it may be re-installed in its respective operating environment and used for a set time or number of cycles (Np). After Np, the gauge is once again inspected to determine the amount of gauge reaction (Ri+p) after the predetermined number of cycles Np.

Bearing in mind that V is a relationship between ΔR and ΔN, once a known change of reaction and corresponding number of cycles Np are obtained a value for (Vdet) may be determined by applying the formula:

$$\frac{R_{i+p} - R_i}{N_p} = V_{det}$$

Comparing $V_{det}$ with the known loading curves allows one to select that loading curve which is closest to matching curve $T_m$ having a $V_m$ most closely matching $V_{det}$.

Knowing which loading curve applies (Tm), one can determine from the graph of FIG. 10 how many elapsed cycles (Ne) would correspond to Ri+p on the load curve Tm. The chart/graph of FIG. 11 may then be utilized for determining the anticipated number of cycles to failure (Nfm) for the load (Tm) The remaining part life (Nr) is then the number of cycles to failure (Nfm) less the number of cycles already elapsed (Ne). This may be expressed by the formula:

$$N_{fm} - N_e = N_r$$

Although number of cycles (N) has been most often referred to above, it will be appreciated that in some instances time may be utilized as an indicator. In the case of a machine part, the number of loading cycles N will be a function of how long the machine is continually operated (as opposed to simply how long the part has been in service). Operating the machine stresses or loads the part 30 cyclically, in other words, a number of cycles per unit time. As time and number of cycles are related, in such a case, either can be used for the testing and calibration.

FIGS. 13-18 are a further example which illustrate change in reflectivity (R1-R6 respectively) of a gauge 30 made of composite material with increasing numbers of loading cycles (N1→N6 respectively).

The above description is intended to be illustrative rather than restrictive. Variations to the exact examples or methodology set out may be apparent to those skilled in the relevant art while remaining within the scope of the invention as defined by the claims set out below.

The invention claimed is:

1. A method for determining the extent of cyclic stress fatigue suffered by a component comprising the steps of:
    (i) providing a strain gauge whose surface undergoes a decrease in reflectivity in response to application of repeated strain cycles to the gauge, the strain gauge comprising a gauge material which undergoes a continued progressive/cumulative and quantifiable decrease in reflectivity in response to repeated strain cycles applied to said gauge material said decrease in reflectivity of the gauge material being indicative of both the degree of strain and the number of cycles incurred during said repeated strain cycles;
    (ii) determining a correlation between the extent of the decrease in reflectivity of the surface of the strain gauge and the effect on said component of the corresponding number and degree of strain cycles;
    (iii) affixing said strain gauge to said component to subject said strain gauge to any strain encountered by an adjacent portion of said component;
    (iv) at least periodically determining said decrease in reflectivity of said strain gauge to determine said extent of cyclic stress fatigue of said component.

2. A method according to claim 1 wherein step (ii) is carried out by:
    (ii-a) applying a strain gauge to a test part;
    (ii-b) cyclically applying a first known load (T) to said test part and monitoring the total number of load cycles (N);
    (ii-c) examining said strain gauge after step (ii-b) and determining and recording the amount of reaction (R) of said strain gauge;
    (ii-d) repeating (ii-b) and (ii-c) for further load cycles;
    (ii-e) determining the relationship between change in number of cycles (N) and amount of change in strain gauge reaction (ΔR) according to the formula:

$$\frac{\Delta R}{N} = V_1$$

where $V_1$ represents the relationship between N and ΔR at load $T_1$;
    (ii-f) continuing to apply, after step (ii-e), said cyclical loading to said part until part failure and recording the number of cycles until failure ($N_{f1}$);
    (ii-g) repeating (ii-a) to (ii-f) for different loads $T_2 \rightarrow T_x$, an additional test part being used for each load, and determining the relationship ($V_2 \rightarrow V_x$) between change in strain gauge reaction (ΔR) and the number of loading cycles (N) to establish known correlations and to establish the number of cycles to failure at each load ($N_{f2} \rightarrow N_{fx}$).

3. The method of claim 1 or 2 wherein step (iv) is carried out by:
    (iv-a) inspecting said strain gauge and determining the amount of strain gauge reaction at the time of inspection ($R_i$);
    (iv-b) loading said part for a predetermined number of loading cycles (Np);
    (iv-c) inspecting said strain gauge after (iv-b) and determining the amount of strain gauge reaction ($R_{i+p}$);

(iv-d) determining the relationship ($V_{det}$) between change in strain gauge reaction ($R_{i+p} - R_i$) and the number of known loading cycles (Np) according to the formula:

$$\frac{R_{i+p} - R_i}{N_p} = \frac{\Delta R}{N_p} = V_{det}$$

(iv-e) comparing the relationship ($V_{det}$) in step (iv-d) with known correlations for the part ($V_1 - V_x$) and selecting the closest to matching known correlations ($V_m$);

(iv-f) determining from said selected correlation ($V_m$) the load ($T_m$) corresponding thereto;

(iv-g) determining from said elected correlation ($V_m$), the number of elapsed cycles ($N_e$) corresponding to the strain gauge reaction ($R_{i+p}$) in step (iv-c);

(iv-h) determining from said selected correlation the number of cycles to failure ($N_{fm}$) at the load ($T_m$) determined in step (iv-f);

(iv-i) subtracting the results ($N_e$) in step (iv-g) from the results ($N_{fm}$) in step (iv-h) to determine the number of remaining cycles ($N_r$) ($N_{fm} - N_e = Nr$).

4. A method according to claim 1 or 2 wherein said part has experienced a known number of cycles at inspection ($N_i$) and wherein step (iv) is carried out by:

(iv-i) inspecting the strain gauge and determining the amount of strain gauge reaction at the time of inspection (Ri);

(iv-ii) determining from the known correlations the load (Tm) corresponding to the amount of strain gauge reaction at the time of inspection ($R_i$) and the known number of cycles ($N_i$);

(iv-iii) determining from the known correlations the number of cycles to failure ($N_{fm}$) at the respective load ($T_m$); and, (iv-iv) subtracting the known number of cycles ($N_i$) from the number of cycles to failure ($N_{fm}$) to determine the number of remaining cycles (Nr) ($N_{fm} - N_i = N_r$).

5. The method of claim 1, wherein the gauge material is a reflective coating.

6. The method of claim 5, wherein the strain gauge further comprises a substrate, the reflective coating being attached to the substrate.

7. The method of claim 5, wherein the reflective coating is a metal coating.

8. The method of claim 7, wherein the metal coating thickness is 10 to 15 microns.

* * * * *